Oct. 15, 1940. S. HAHN Plant Pat. 429
IVY PLANT
Filed Feb. 12, 1940
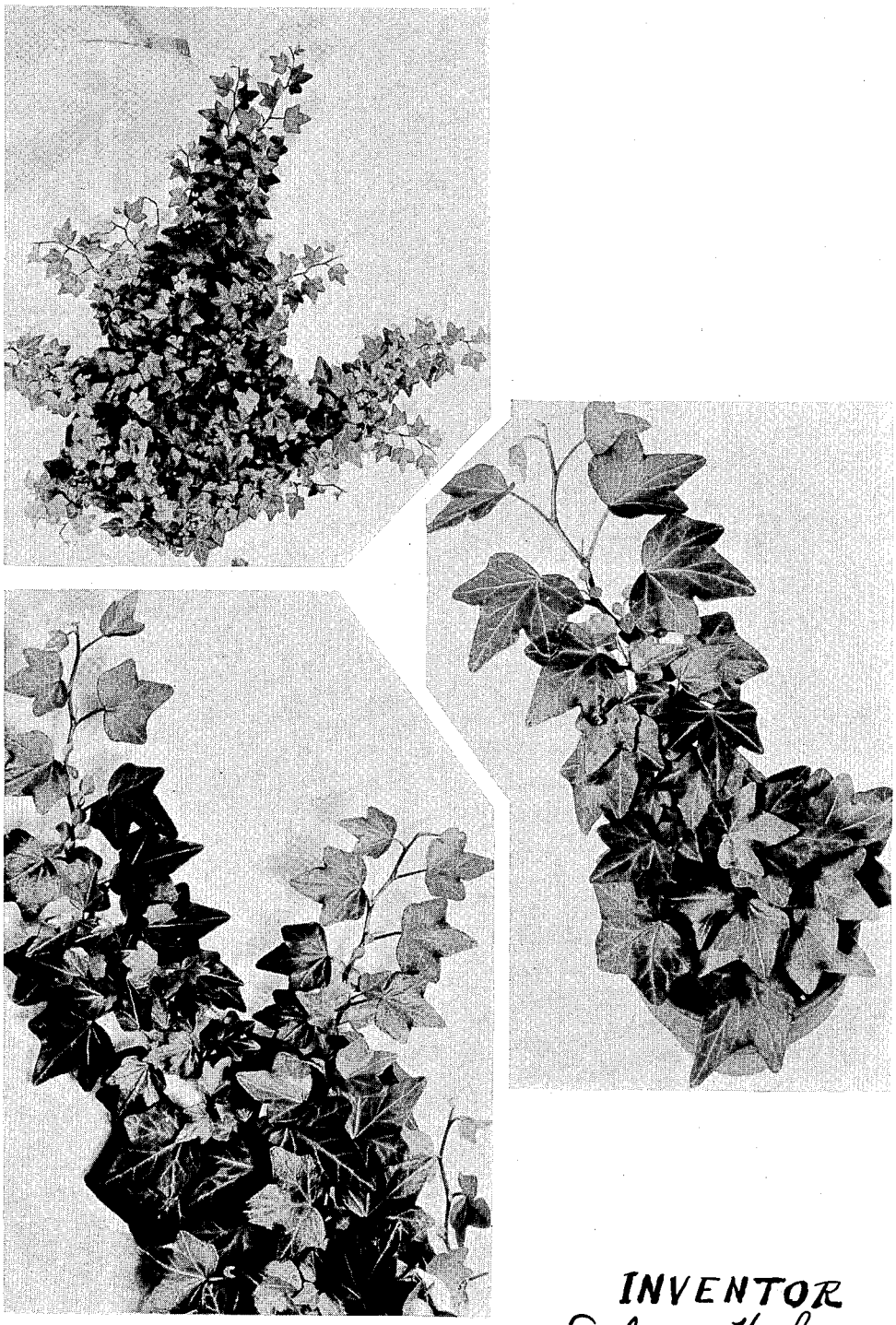
INVENTOR
Sylvan Hahn
By Orville M. Kile
Plant Patent Agent Patented Oct. 15, 1940

Plant Pat. 429

UNITED STATES PATENT OFFICE

429

IVY PLANT

Sylvan Hahn, Pittsburgh, Pa.

Application February 12, 1940, Serial No. 318,576

1 Claim. (Cl. 47—59)

My new variety of ivy was discovered by me growing as a sporting branch on a plant of Hahn's Self-branching Ivy and has been reproduced by means of cuttings for several years.

The illustrations accompanying this application show three views of this variety of ivy, in varying stages of development—a single, month-old spray or plant, a three-month plant, and a plant about six months old. The larger and older specimen shows particularly the compactness of growth of this variety. The three-month specimen shows particularly the short nodes and self-branching shoots.

This variety is of the class having medium to small leaves and is in several respects an improvement over other varieties in this class, particularly its compact growth and habit of self-branching.

It is of rapid, compact growth and produces by natural means, plants which are extremely bushy. Contributing to this bushy and compact growth habit are several features as follows: (1) The variety is freely self-branching without cutting or trimming; (2) the stem nodes are very short, allowing the foliage to be very closely set on the stems—one leaf almost overlapping the next on a stem; (3) the leaf stems are short, making the leaves cling close to the main stem.

The leaves are not extremely small but are what might be termed medium small as compared to other varieties grown under the same conditions. The actual measurements of the leaf will vary with soil, moisture and climatic conditions. The shape of the leaf is radiate or of somewhat maple-leaf form, having three prominent lobes and, on mature leaves, two less prominent lobes. In mature leaves the veining is prominently raised (varix) and considerably lighter in color than the rest of the leaf. They are leathery and of good substance, which quality gives them much more durability when grown indoors where conditions are unfavorable.

Because of the compactness and freedom of growth and the medium size of the leaves, this variety is particularly well adapted to use as an individual pot plant or for dish gardens.

Having thus disclosed my discovery, I claim:

A new and distinct variety of ivy plant characterized particularly by its medium small, radiate leaves with varix veins and short petioles; its short nodes; its rapid bushy and compact growth; and its habit of branching freely without trimming.

SYLVAN HAHN.